US00PP11493P

United States Patent [19]

Werner et al.

[11] Patent Number: Plant 11,493

[45] Date of Patent: Aug. 22, 2000

[54] PEACH TREE NAMED 'CORINTHIAN WHITE'

[76] Inventors: Dennis James Werner, 268 Kilgore Hall, Horticultural Science Department, North Carolina State University; Steve Martin Worthington; Layne Karlton Snelling, both of 59 Kilgore Hall, Horticultural Science Department, North Carolina State University, all of Raleigh, N.C. 27695-7609

[21] Appl. No.: 09/146,219

[22] Filed: Sep. 2, 1998

[51] Int. Cl.[7] ..... A01H 5/00

[52] U.S. Cl. ..... Plt./196

[58] Field of Search ..... Plt./194, 187, 199, Plt./191, 180, 196

*Primary Examiner*—Howard J. Locker
*Assistant Examiner*—Wendy A Baker

[57] ABSTRACT

A new and distinct cultivar of ornamental peach tree called 'Corinthian White' is provided that demonstrates a narrowly columnar growth habit, a vigorous growth rate, green foliage, bright green new stems, and an abundance of white-colored, double flowers. The new cultivar produces very few fruit, and is intended for use as a Spring flowering ornamental plant in the home landscape.

1 Drawing Sheet

SUMMARY OF THE INVENTION

The new and distinct variety of peach (*Prunus persica* (L.) Batsch) originated as a second generation descendant from a hand pollinated cross of North Carolina selection 'NC174RL' nectarine (non-patented)×a selection of Japanese 'Pillar' peach made in 1983 at the Sandhills Research Station at Jackson Springs, N.C. The parent plants used in this hybridization have not been named and released and are unavailable in commerce.

The seeds resulting from this controlled hybridization were germinated in a greenhouse at North Carolina State University, Raleigh, N.C. in the Fall of 1983 and planted in the field in Spring of 1984. These trees were grown to maturity; trees were self pollinated in Spring of 1988, and the resultant seed was harvested in August 1988. This seed was sown directly in the field in November 1988, and seedlings flowered in 1991. One seedling, designated NC174RL×Pil-64, was selected for its green foliage color, narrowly columnar growth habit, and heavy production of pure white double flowers.

During 1993 and 1996, the original plant selection was propagated asexually by grafting of vegetative buds onto peach seedling rootstock, cultivar 'Lovell', at the Sandhills Research Station. A grafted tree of the variety was established at the North Carolina State University Lake Wheeler Field Laboratory Research Station in Raleigh, N.C. Subsequently, a larger test planting has been established with asexually multiplied plants at the Sandhills Research Station, at the above noted location.

The new variety has routinely been asexually multiplied by grafting, specifically 'T' and chip budding. It readily forms a graft union with 'Lovell' peach rootstock and resumes normal growth. During all asexual propagation, the characteristics of the original plant have been maintained and no aberrant phenotypes have appeared. There is no substantial difference in tree performance or phenotype between trees grown on their own roots as compared to trees grafted on 'Lovell' seedling rootstock.

Test plantings at the two research station locations noted above, which vary considerably in soil and climatic conditions, demonstrate this variety to be widely adapted to differing soil and climatic conditions.

Plants and fruit of this new variety differ phenotypically from its parents. The new variety produces pure white double flowers, differing from the single pink flowers of 'NC174RL' and the double pink and white variegated flowers of the Japanese 'Pillar' peach parent. Leaf color is green, growth habit is narrowly columnar, and fruit are pubescent (peach), distinguishing it from the 'NC174RL' nectarine parent. Fruit of this new variety are small and of poor eating quality, and are judged to be of no commercial importance.

Plants of the new variety are very vigorous and grow rapidly after establishment of trees in the field. Young trees have averaged 3–4 feet of growth per year. A four-year-old tree measured in Raleigh, N.C. was 14.7 feet in height and 4.7 feet in spread, with spread measured 6 feet from ground level. Trunk diameter (girth) was 4.2 inches, measured one foot from ground level. Plants are narrowly columnar in growth habit. The branch angles between the trunk and lateral branches of 'Corinthian White' measure between 5 to 20 degrees, in comparison to non-columnar peach varieties such as 'Contender', which typically measure between 35 to 50 degrees.

Flowering sometimes occurs in the second year of growth, but more commonly trees begin flowering in the third year after establishment. Flowers are fully double, pure white, and very attractive. Flowering usually begins in mid to late March in Raleigh, N.C.; the date of first bloom typically occurs from March 15 to March 30. Full bloom typically occurs from March 25 to April 10, depending on weather conditions. Bloom duration is typically 10–14 days, and individual flowers last about 7–10 days, depending on temperature during bloom. The chilling requirement is estimated to be 950 hours below 4 C., based on comparison of flowering time to peach varieties 'Contender', 'Winblo', and 'Clayton' at the Raleigh, N.C. test location.

Fertility of flowers is poor, and fruit set is generally low in most years. It is estimated that less than 1% of flowers produced set fruit. Fruit are very small, bitter tasting, and of no horticultural importance. Fruit ripen in mid to late August in Raleigh, N.C.

The new variety has been named the Corinthian White cultivar.

BRIEF DESCRIPTION OF THE DRAWINGS

The accompanying photographs show typical specimens of the entire tree during and after flowering, and close-up pictures of the flowers in color as nearly true as it is reasonably possible to make in a color illustration of this character.

DETAILED DESCRIPTION OF THE NEW VARIETY

Figure 1:
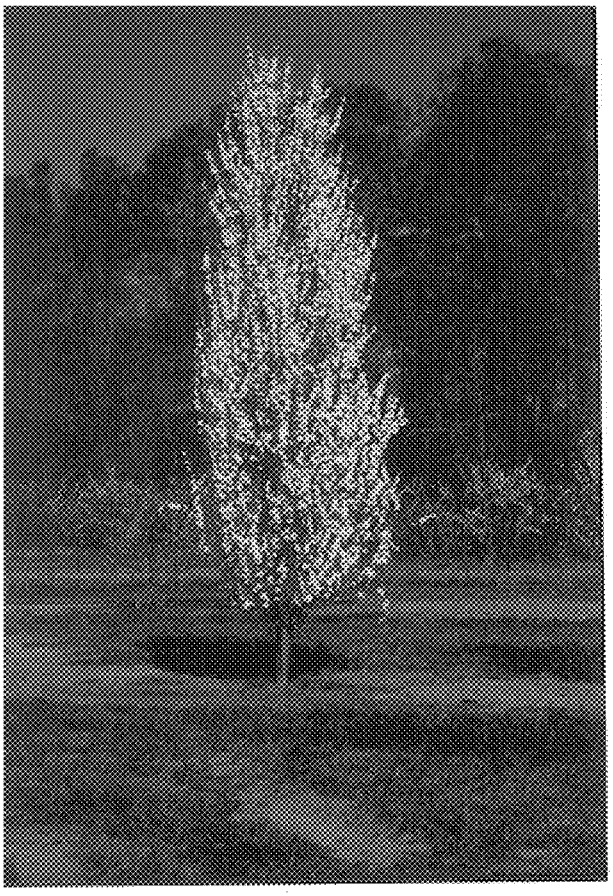
FIG. 1 shows a four-year-old tree of 'Corinthian White' in full bloom at Raleigh, N.C., showing the narrowly columnar tree architecture, flower color, and heavy flowering characteristics.
Figure 2:
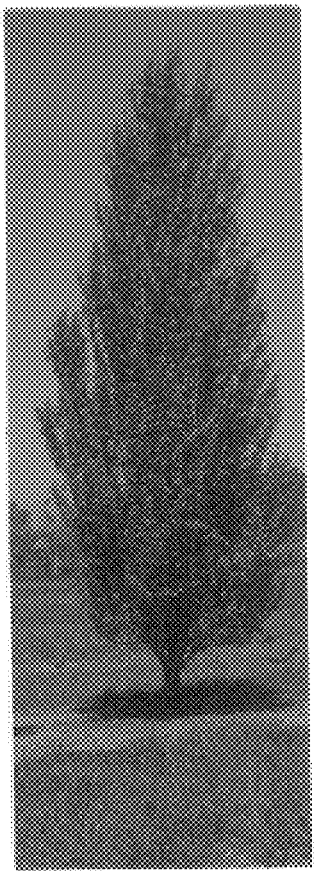
FIG. 2 shows a four-year-old tree of 'Corinthian White' taken after flowering, showing the upright tree architecture and the overall foliage color.
Figure 3:
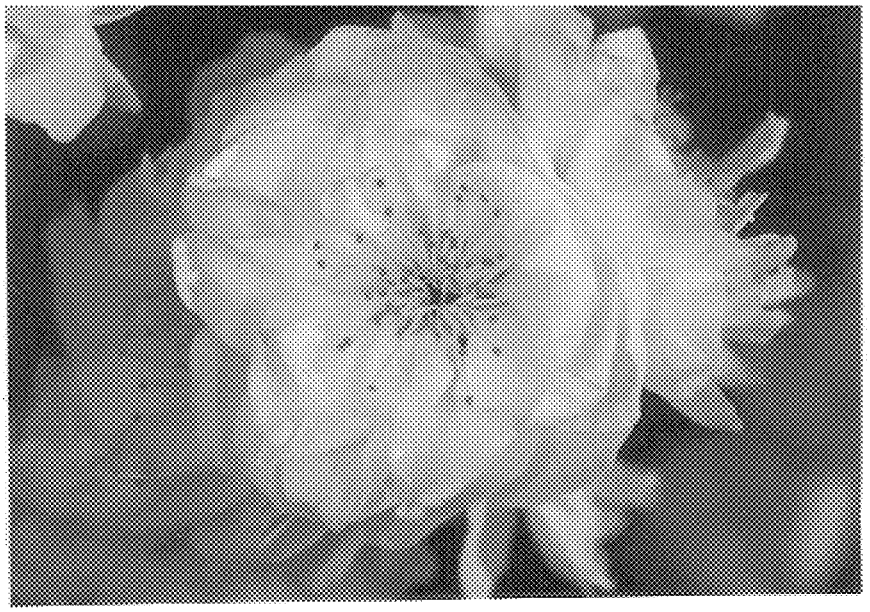
FIG. 3 shows a close up photograph of the flower of 'Corinthian White', showing the double flower structure, and the white flower color.

The following is a detailed description of the botanical and pomological characteristics of the subject peach. Color data are presented in The Royal Horticultural Society Colour chart designations. Where dimensions, sizes, colors and other characteristics are given, it is to be understood that such characteristics are approximations of averages set forth as accurately as practicable.

The descriptions reported herein are from specimens grown at Raleigh, N.C. unless otherwise noted.

Tree:
- *Size*.—Large. 14–16 ft. height after four years of growth.
- *Vigor*.—Very vigorous.
- *Growth*.—Narrowly columnar.
- *Fruit production*.—Low.
- *Pest resistance*.—Susceptible to peach tree borer, moderately resistant to bacterial leaf spot (Sandhills Research Station observations).

Trunk:
- *Size*.—Medium.
- *Texture*.—Medium to rough.
- *Color*.—Gray-green (197-B).

Branches:
- *Size*.—Medium.
- *Surface*.—Smooth (new) to medium rough (old).
- *Lenticels*.—Medium size. Medium number.
- *Color*.—Bright green (actively growing new growth). Dormant one-year-old shoots yellow-green (145-B). Dormant two-year-old shoots gray-brown (199-A). Lacking any red color.

Foliage:
- *Leaves*.—Large. Mature leaf length 13.4 cm; width 4.5 cm.
- *Form*.—Lanceolate. Acutely pointed. Leaf base medium pointed, cuneate.
- *Thickness*.—Medium.
- *Texture*.—Smooth to slightly rugose.
- *Margin*.—Crenate.
- *Petiole*.—Medium length, light to medium green.
- *Stipules*.—Present. Small.
- *Pubescence*.—Absent on both lower and upper surface.
- *Venation*.—Pinnate.
- *Glands*.—Average number 3. Varies from 2 to 5. Located on base of leaf and upper portion of petiole. Reinform.
- *Color*.—Upper surface — green to deep green (137A). Lower surface — dull green (137C).
- *Density*.—Dense.

Flower buds:
- *Size*.—Large.
- *Length*.—Medium.
- *Shape*.—Plump, slightly tapered at apex. Typical of peach.
- *Color*.—Light brown.

Flowers:
- *Date of first bloom*.—March 15 to March 30. Varies yearly due to weather conditions.
- *Date of full bloom*.—March 25 to April 10. Varies yearly due to weather conditions.
- *Size*.—Large, double, showy. Mean diameter of 5 typical flowers is 39 mm.
- *Pedicel length*.—14 mm.
- *Color*.—White, with no evidence of pink variegation (155D).
- *Calyx Color*.—R.H.S. 144B.
- *Reproductive organs*.—Stamens — erect, numerous. Pistils — usually one. Pollen — normal and abundant. Bright yellow.
- *Number of flowers per bud*.—One.
- *Number of petals per flower*.—Average 23.
- *Fertility*.—Self-fertile.

Fruit:
- *Maturity*.—Late. Mid to late August.
- *Size*.—Very small. Less than 1.5 cm diameter.
- *Form*.—Slightly oblong.
- *Suture*.—Shallow.
- *Pubescence*.—Heavy.
- *Skin color*.—Yellowish-green with no red.
- *Flesh color*.—White.
- *Stone*.—Small, freestone.
- *Eating quality*.—Very poor.
- *Uses*.—None.

The variety: The most distinctive features of the variety are its narrowly columnar growth habit, and its double (multiple petals) white flowers.

We claim:

1. A new and distinct variety of ornamental peach tree, substantially as illustrated and described, characterized by its narrowly columnar growth habit and large double white flowers.

* * * * *